(12) United States Patent
Shevgoor (10) Patent No.: US 12,038,772 B2
(45) Date of Patent: Jul. 16, 2024

(54) DIAPHRAGM CHECK VALVE

(71) Applicant: CareFusion 303, Inc., San Diego, CA (US)

(72) Inventor: Siddarth K. Shevgoor, Laguna Beach, CA (US)

(73) Assignee: CAREFUSION 303, INC., San Diego, CA (US)

( * ) Notice: Subject to any disclaimer, the term of this patent is extended or adjusted under 35 U.S.C. 154(b) by 0 days.

(21) Appl. No.: 18/454,952

(22) Filed: Aug. 24, 2023

(65) Prior Publication Data

US 2023/0393592 A1    Dec. 7, 2023

Related U.S. Application Data

(63) Continuation of application No. 17/687,530, filed on Mar. 4, 2022, now Pat. No. 11,774,988, which is a
(Continued)

(51) Int. Cl.
*F16K 15/14*     (2006.01)
*F16K 7/17*      (2006.01)
(Continued)

(52) U.S. Cl.
CPC .............. *G05D 7/0113* (2013.01); *F16K 7/17* (2013.01); *F16K 15/147* (2013.01);
(Continued)

(58) Field of Classification Search
CPC .. F16K 15/145; F16K 15/147; F16K 15/1471; F16K 27/0236; Y10T 137/788;
(Continued)

(56) References Cited

U.S. PATENT DOCUMENTS 2,646,063 A * 7/1953 Hayes .................. F16K 15/144
                                                       137/859
3,422,844 A    1/1969 Grise
(Continued)

FOREIGN PATENT DOCUMENTS

CH          344883        2/1960
CN       101272865 A      9/2008
(Continued)

OTHER PUBLICATIONS

Australian Office Action for Application No. 2018366035, dated Sep. 6, 2023, 3 pages.
(Continued)

*Primary Examiner* — Hailey K. Do
(74) *Attorney, Agent, or Firm* — Morgan, Lewis & Bockius LLP (57) ABSTRACT

A check valve, including a valve and a valve support surface, to permit a fluid to move through the check valve in a first direction and resist a fluid flow through the valve in a second direction, the valve having a valve diaphragm and an isolating bridge, with a portion of the valve engaging against valve support surface to resist deformation or stretching of the valve when a backflow of fluid into the check valve occurs. The valve support surface having a first surface portion and a second surface portion, and the valve positioned with the valve diaphragm spaced apart from the first surface portion, and the isolating bridge spaced apart from the second surface portion.

20 Claims, 7 Drawing Sheets

Related U.S. Application Data continuation of application No. 16/810,605, filed on Mar. 5, 2020, now Pat. No. 11,269,360, which is a continuation of application No. 15/807,505, filed on Nov. 8, 2017, now Pat. No. 10,591,932.

(51) Int. Cl.
*F16K 27/02* (2006.01)
*F16K 31/126* (2006.01)
*G05D 7/01* (2006.01)
*A61M 39/24* (2006.01)

(52) U.S. Cl.
CPC ........ *F16K 27/0236* (2013.01); *F16K 31/126* (2013.01); *G05D 7/012* (2013.01); *A61M 2039/2426* (2013.01); *A61M 2039/246* (2013.01)

(58) Field of Classification Search
CPC ....... Y10T 137/7881; A61M 2039/246; A61M 2039/2426
See application file for complete search history.

(56) References Cited

U.S. PATENT DOCUMENTS

| | | | |
|---|---|---|---|
| 4,129,143 | A | 12/1978 | Hoffman |
| 4,143,853 | A | 3/1979 | Abramson |
| 4,712,580 | A | 12/1987 | Gilman |
| 5,305,795 | A * | 4/1994 | Forberg ................ F16K 15/144 137/859 |
| 5,873,297 | A | 2/1999 | Stoiic |
| 6,062,435 | A | 5/2000 | Hess |
| 6,749,092 | B2 | 6/2004 | Olechowski |
| 7,950,621 | B2 | 5/2011 | Meinig |
| 8,397,958 | B2 | 3/2013 | Smith |
| 9,682,804 | B2 | 6/2017 | Hatton |
| 2004/0102738 | A1 | 5/2004 | Dikeman |
| 2006/0138163 | A1 | 6/2006 | Danks |
| 2008/0035677 | A1 | 2/2008 | Daansen |
| 2009/0188950 | A1 | 7/2009 | Gaus |
| 2010/0089921 | A1 | 4/2010 | Ellenkamp |
| 2010/0193516 | A1 | 8/2010 | LaBean |
| 2016/0279404 | A1 | 9/2016 | Nelson |
| 2017/0066563 | A1 | 3/2017 | Geiger |

FOREIGN PATENT DOCUMENTS

| | | |
|---|---|---|
| CN | 201267678 Y | 7/2009 |
| CN | 101808692 A | 8/2010 |
| CN | 102481427 A | 5/2012 |
| CN | 102512731 A | 6/2012 |
| DE | 202006016730 U1 | 1/2007 |
| DE | 202008009245 U1 | 9/2008 |
| DE | 102013005624 A1 | 10/2013 |
| EP | 1897585 A1 | 3/2008 |
| EP | 2679273 A1 | 1/2014 |
| FR | 2436309 A1 | 4/1980 |
| FR | 2666745 A1 | 3/1992 |
| JP | S60128072 U | 8/1985 |
| JP | 2017030846 A | 2/2017 |
| WO | WO-9534500 A1 | 12/1995 |
| WO | WO-2017074420 A1 | 5/2017 |
| WO | WO-2017087686 A1 | 5/2017 |

OTHER PUBLICATIONS

Chinese Office Action for Application No. 201880072091.6, dated Sep. 24, 2021, 21 pages including translation.
European Office Action for Application No. 18808180.6, dated Jun. 23, 2021, 4 pages.
Extended European Search Report for Application No. 23176717.9, dated Sep. 11, 2023, 14 pages.
International Preliminary Report on Patentability from the IPEA for Application No. PCT/US2018/059653, dated Jan. 1, 2020, 17 pages.
International Search Report and Written Opinion for Application No. PCT/US2018/059653, dated Feb. 11, 2019, 15 pages.
Japanese Office Action in Application No. 2020-524895 dated Dec. 6, 2022, 9 pages including translation.
Written Opinion of the International Preliminary Examining Authority for Application No. PCT/US2018/059653, dated Sep. 24, 2019, 8 pages.
Japanese Office Action in Application No. 2023-109098, dated May 1, 2024, 9 pages including translation.

* cited by examiner

DIAPHRAGM CHECK VALVE

CROSS-REFERENCE TO RELATED APPLICATIONS

This application is a continuation of U.S. patent application Ser. No. 17/687,530, filed Mar. 4, 2022, titled DIAPHRAGM CHECK VALVE, which is a continuation of U.S. patent application Ser. No. 16/810,605, filed Mar. 5, 2020, now U.S. Pat. No. 11,269,360, titled DIAPHRAGM CHECK VALVE, which is a continuation of U.S. patent application Ser. No. 15/807,505, filed Nov. 8, 2017, now U.S. Pat. No. 10,591,932, titled DIAPHRAGM CHECK VALVE, the disclosure of each of which is incorporated herein by reference in its entirety.

BACKGROUND

The present disclosure relates to controlling the direction of a fluid flow. More specifically, the present descriptions relate to control of fluid flow using check valves.

Check valves are one-way valves that permit a fluid to move through a valve in a first direction and restrict a backflow fluid flow through the valve in a second direction, which is generally different than the first direction.

Check valves can be used in many types of application, including, pumps, such as piston-driven and diaphragm pumps; fluid systems for industrial processes, including chemical and power plants; fluid control systems, such as irrigation sprinklers and drip irrigation; and in medical applications, such as check valves for the heart ventricles, and intravenous fluid delivery.

A check valve can include a valve that is generally shaped as a flat disk forming a diaphragm. The diaphragm can have a slit forming one or more valve segment. The valve segments can engage against each other in a closed position to resist fluid flow through the valve, and the valve segments can move, relative to each other, to open the valve and permit a fluid flow through the valve.

Check valves can have a normally-closed configuration where the valve is in a closed position to resist fluid flow through the valve. The check valve can move to an open position to permit fluid therethrough by a fluid pressure or engagement of a fluid against the valve. The pressure or force required to move the valve to the open position is known as the cracking pressure. The cracking pressure can be a pressure at the inlet, e.g., upstream, of the check valve at which a first indication of flow through the valve occurs. In some check valves, the valve is moved to an open position when a positive pressure differential is applied to the valve, for example, when a pressure upstream of the valve is greater than a pressure downstream of the valve.

In the open position, a check valve can permit fluid flow through the valve with minimal pressure loss. The check valve can move to the closed position when the positive pressure differential is decreased, removed, or reversed. In some instances, the inherent resilience of the valve enables the valve to move to the closed position. A negative pressure differential, e.g., when the fluid pressure downstream of the valve is greater than the fluid pressure upstream of the valve, can cause the valve to move to the closed position. In the closed position, a check valve can resist a backflow of fluid of at least 30 psi.

SUMMARY

A check valve can fail to function as intended when the valve does not move to the closed position or does not resist a backflow of fluid. A check valve can fail to move to the closed position or resist a backflow of fluid when a particulate or debris becomes lodged in the valve or another portion of the check valve.

Fluid pressure caused by fluid backflow acting upon the valve can cause a portion of the valve to move into or engage against the housing or a retention feature, thereby causing the valve to stretch, thereby forming a gap between the valve segments or effecting intended operation of the check valve.

Further, failure of a check valve to function as intended can also be caused by engagement of the valve with a housing or other valve retention structure. The coupling of a valve with a housing may include a portion of the valve being compressed axially. For example, an outer perimeter or rim of the valve can be axially compressed. The axial compression may direct a force toward the valve segments, causing the valve segments to buckle or tent, thereby forming a gap between the valve segments. Axial compression of the valve may also create a force radially outward, causing the valve or valve segments to be pulled apart, thereby forming a gap between the valve segments.

Axial or radial force, directed toward the valve, can be adjusted to achieve a desired performance characteristic of the check valve. However, the axial or radial force can increase the cracking pressure beyond the intended value. For example, a 0.5 inch valve having a 0.25 inch diameter across the valve diaphragm can optimally seal with approximately 0.0001 to 0.001 of radial compression of the valve. However, radial compression in excess of 0.001 inch may begin to adversely affect sealing between the valve segments causing the valve to tent or form a passage therethrough. Practical manufacturing tolerances for a valve can be approximately 0.001 to 0.002 inch. If manufacturing tolerances for any portion of a valve, a valve housing, and retention feature are included, the combined variance in radial compression may be between about 0.002 to 0.004 inch, which can adversely affect sealing between the valve segments. Manufacturing is further complicated when considering that maintaining manufacturing tolerances of less than 0.001 inch may increase manufacturing costs, manufacturing effort, and increase the rate of nonconforming check valves.

Other causes for a check valve failing to function as intended include, gaps formed in or between the valve segments as a result of manufacturing procedures, including, for example, operations to create slits through the valve diaphragm. Additionally, a check valve can fail to function as intended include when the valve is not seated or coupled with the housing as intended by the check valve design.

In accordance with at least some embodiments disclosed herein is the realization that although check valves can be design with specific performance characteristics, certain problems can occur with manufacturing, assembly, and use of the check valve. For example, manufacturing variances can change the performance or operation of a check valve, a check valve can be manufactured or assembled incorrectly, and debris from manufacturing or a fluid flow can become lodged in the check valve.

An aspect of the present disclosure provides a check valve assembly comprising: a valve support surface having a first support surface and a second support surface, the second support surface positioned radially outward, relative to the first support surface; and a valve having: a mounting rim; a valve diaphragm extending radially inward from the mounting rim, and having a valve segment defined by a slit; and an annular isolating bridge extending between the mounting rim and the valve diaphragm; wherein a distance from the first support surface to the nearest surface of the valve diaphragm is greater than a distance from the second support surface to the nearest surface of the annular isolating bridge.

Some instances of the present disclosure provide a method of controlling flow through a check valve assembly comprising: defining a fluid passageway having a valve support surface, wherein the valve support surface comprises a first support surface and a second support surface, the second support surface radially outward, relative to the first support surface; positioning a valve adjacent to the valve support surface, wherein the valve comprises a valve diaphragm configured to resist a fluid flow through the fluid passageway, the valve diaphragm having a valve segment defined by a slit, and an annular isolating bridge extending radially outward from the valve diaphragm; wherein, when the valve is moved toward the valve support surface, the isolating bridge engages the second support surface before the valve diaphragm engages the first support surface.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments are described below with reference to the drawings. The illustrated embodiments are intended to illustrate, but not to limit, the disclosure. The drawings contain the following figures.

DETAILED DESCRIPTION

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with similar element numbers for ease of understanding.

In accordance with at least some embodiments disclosed herein is a check valve that can resist buckling or tenting of the valve by reducing the transfer of forces, including axial and radial forces, from a housing or valve retention feature toward the valve. For example, the force transferred to the valve diaphragm can be reduced, such that the valve diaphragm is sealed to resist fluid flow through the valve, yet the valve diaphragm does not buckle or tent. Additionally, features of at least some embodiments of the diaphragm check valve of the present disclosure can reduce cracking pressure of the valve.

In at least some embodiments disclosed herein, the device of the present disclosure can resist movement of a valve to prevent unintended stretching or contact of the valve against the housing or other portion of the check valve. Further, at least some embodiments disclosed herein provide a check valve having reduced manufacturing complexity and reduced tolerance requirements.

Figure 1:
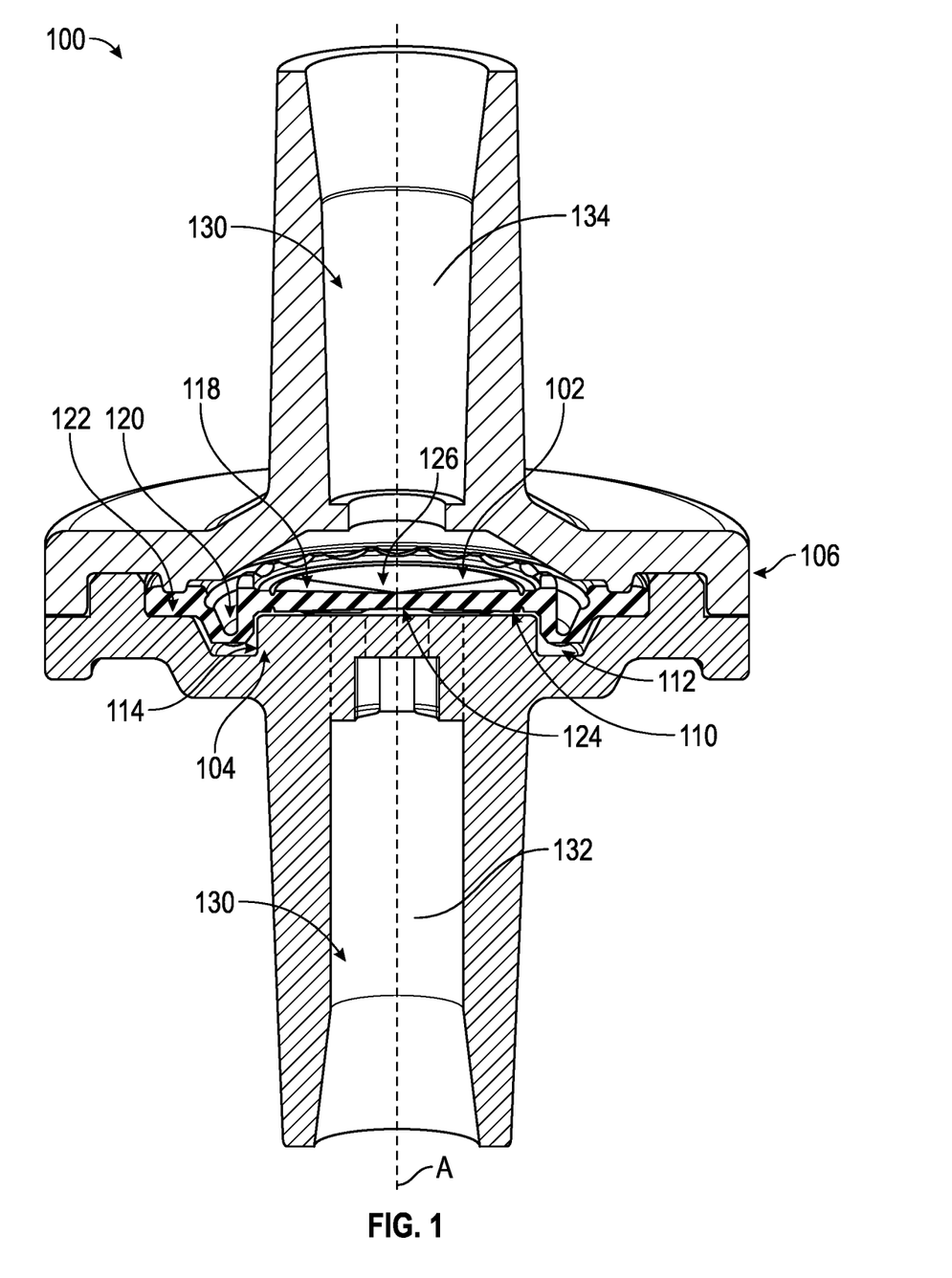
FIG. 1 is a cross-sectional perspective view of a diaphragm check valve, according to some embodiments.

FIG. 1 illustrates a cross-sectional view of a diaphragm check valve 100 according to some embodiments of the present disclosure. The check valve 100 can comprise a valve 102 and a valve support surface 104. Optionally, a valve housing 106 can comprise the valve support surface 104. It should be understood that although the present disclosure includes reference to a housing 106, the valve support surface 104 can be formed as a portion of another structure adjacent to the valve 102. For example, the valve support surface 104 can be formed as a separate component positioned within a fluid pathway and adjacent to a valve. The valve support surface 104 can be associated with a fluid pathway of a device such as a pump, or within a heart ventricle. In another example, the valve support surface 104 can be formed as a portion of a surface in a device, such as a pump. In yet another example, the valve support surface 104 can be formed as a portion of the valve.

The valve 102 and the valve support surface 104 are positioned relative to each other so that a portion of the valve 102 can engage against the valve support surface 104 during at least a portion of operation of the valve. For example, the valve 102 and the valve support surface 104 can be oriented relative to each other so that a portion of the valve engages against the valve support surface 104 when the valve 102 is in an open position to permit fluid to move through the check valve 100. The valve 102 and the valve support surface 104 can also be oriented relative to each other so that a portion of the valve 102 engages against the valve support surface 104 when the valve 102 is in a closed positon to restrict movement of fluid through the check valve 100.

The valve support surface 104 can include a first support surface 110 and a second support surface 112. The first support surface 110 and the second support surface 112 are configured to be engaged against by a portion of the valve 102. In some embodiments, the valve support surface 104 can include a third support surface 114 that is engaged against by a portion of the valve 102.

The valve 102 can include a valve diaphragm 118 with a valve segment configured to permit or restrict fluid flow through the valve 102. The valve diaphragm 118 can be shaped as a disk or other planar shape. An isolating bridge 120 can extend away from the valve diaphragm 118. The isolating bridge 120 can extend away from the valve diaphragm 118 in a direction that is relative to a valve axis A that extends through a center of the valve 102. For example, the isolating bridge 120 can extend radially outward from the valve diaphragm 118. In some embodiments, the isolating bridge 120 can extend axially away from the valve diaphragm 118. The isolating bridge 120 can extend in a direction that is any of parallel, perpendicular, and transverse to the valve axis A. Optionally, the valve 102 can include a mounting rim 122 that extends around the valve diaphragm 118. The mounting rim 122 can be positioned, relative to the valve diaphragm 118, so that the isolating bridge 120 extends between the mounting rim 122 and the valve diaphragm 118.

The valve 102 can have a first end portion 124 and a second end portion 126. When the valve 102 is coupled with a fluid passageway, for example, the fluid passageway 130 extends through the housing 106, the first and the second end portion of the valve 102 can be oriented relative to the fluid passageway 130. The valve 102 can be oriented with the fluid passageway 130 to define an upstream portion 132 of the fluid passageway, adjacent to the first end portion 124 of the valve, and a downstream portion 134 fluid passageway, adjacent to the second end portion 126 of the valve. The first end portion 124, e.g., upstream side, of the valve can be engaged against by a fluid flow in the upstream portion 132 of the fluid passageway, and the second end portion 126, e.g., downstream side, of the valve can be engaged against by a fluid flow in the downstream portion 134 of the fluid passageway. Further, any of the first end portion 124 and the second end portion 126 of the valve can be engaged against by a backflow in the fluid passageway 130.

Optionally, the valve 102 can be oriented with the fluid passageway 130 so that the first end portion 124 and the second end portion 126 can be engaged against by any of an upstream and downstream fluid flow. For example, the valve 102 can be coupled with a fluid passageway wherein a fluid flow can change directions.

Figure 2:
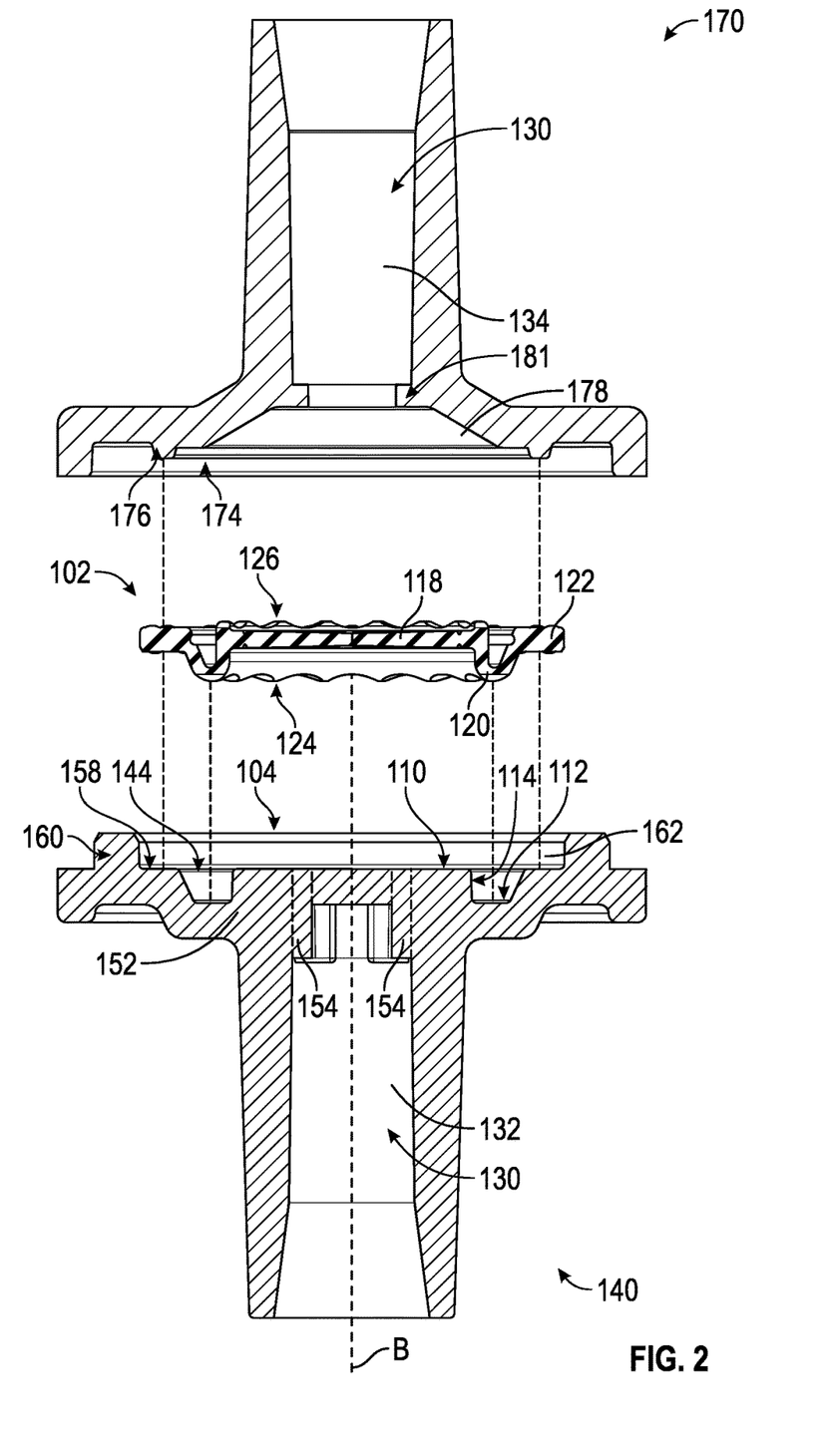
FIG. 2 is a cross-sectional exploded view of a diaphragm check valve, according to some embodiments.

Referring to FIGS. 1 and 2, the valve 102 is oriented adjacent to the valve support surface 104 with the first end portion 124 facing the valve support surface 104. The valve 102 is positioned with the valve diaphragm 118 aligned with the first support surface 110, and the isolating bridge 120 aligned with the second support surface 112. The mounting rim 122 is positioned to align with a retention feature of the valve support surface 104 and/or a valve housing 106.

FIG. 1 illustrates the valve 102 in a closed or neutral position. In the closed position, the valve 102 resists movement of a fluid through the check valve 100. Further, in the closed position, a portion of the valve 102 can be spaced apart from the valve support surface 104. For example, the valve diaphragm 118 can be spaced apart from the first support surface 110, and the isolating bridge 120 can be spaced apart from the second support surface 112. Optionally, the isolating bridge 120 can be spaced apart from the third support surface 114.

When the valve 102 is moved to an open position, the valve segment can permit movement of fluid through the valve 102. In the open position, fluid can move through the valve 102, from the upstream portion 132 of the fluid passageway to the downstream portion 134 of the fluid passageway. The valve 102 can be moved to an open position by positive pressure against the first end portion 124 of the valve, relative to the second end portion 126 of the valve, or negative pressure against the second end portion 126 of the valve, relative to the first end portion 124 of the valve.

When the valve 102 moves to an open position, the valve 102, or portions thereof, can move relative to the valve support surface 104. For example, a portion of the valve diaphragm 118 can move away from the first support surface 110, and can permit a fluid to flow through the valve. A portion of the isolating bridge 120 can move away from the second support surface 112. In some embodiments of the present disclosure, another portion of the isolating bridge 120 can move toward the third support surface 114 when the valve 102 moves toward the open position.

In some instances, a positive pressure against the second end portion 126, relative to the first end portion 124, or a backflow through the downstream portion 134 of the fluid passageway, causes the valve 102 to move toward the closed position. Pressure acting against the valve 102 can cause portions of the valve 102 to move relative to the valve support surface 104. For example, a backflow of fluid engaged against the second end portion 126 can cause a portion of the valve 102 to move toward the first support surface 110. In some embodiments, the valve diaphragm 118 moves toward the first support surface 110, and the isolating bridge 120 moves toward the second support surface 112. In some embodiments of the present disclosure, a portion of the isolating bridge 120 moves away from the third support surface 114.

The check valve 100 can have a valve support surface positioned on any of an upstream portion 132 of the fluid passageway and a downstream portion 134 of the fluid passageway. In some embodiments of the present disclosure, the valve 102 can be positioned with the valve axis A perpendicular or transverse to a direction of flow through the valve 102. In some embodiments, a pre-filter or molded filtering features may be fluidly coupled with the check valve 100 and the fluid passageway. For example, a pre-filter can be positioned upstream or downstream in the passageway relative to the check valve 100.

Figure 3:
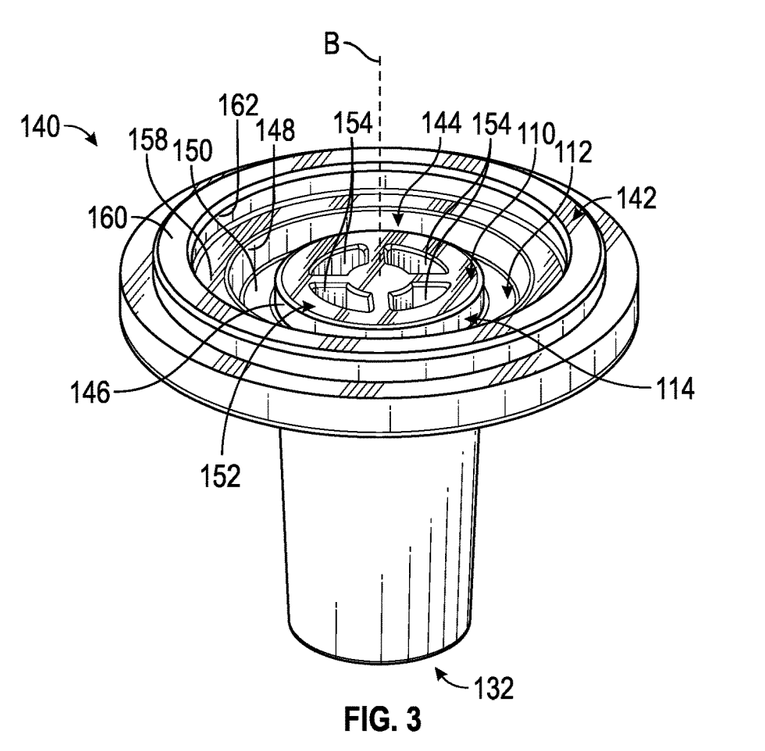
FIG. 3 is a perspective view of a housing of a diaphragm check valve, according to some embodiments.

FIGS. 2-3 illustrate an embodiment of a housing 106 for a check valve. The housing 106 can include an upstream valve housing 140 and a downstream valve housing 170. The upstream valve housing 140 and the downstream valve housing 170 couple together to direct fluid through the check valve 100. Further, the valve 102 can couple with any of the upstream valve housing 140 and the downstream valve housing 170 to retain the valve 102 with the check valve 100, and to prevent movement of the valve mounting rim 122 relative to a portion of the housing 106. In some embodiments of the present disclosure, the check valve can include a unitary or monolithic housing, or a housing having one or more portions coupled or formed together.

The upstream valve housing 140 is shaped as a body having an end portion 142 and defining a fluid passage 130. The fluid passage can comprise the upstream portion 132 of the passageway that extends through the end portion 142.

The upstream portion 132 of the passageway defines an upstream housing axis B. A fluid moving through the upstream portion 132 of the passageway is directed toward or away from the upstream housing end 142.

The upstream valve housing 140 includes the valve support surface 104, or a portion thereof. The valve support surface 104 is defined by the end portion 142 of the upstream valve housing 140. The valve support surface 104 includes an annular channel 144 that extends into the upstream valve housing 140. The annular channel 144 can be shaped as a toroid that extends around the upstream valve housing axis B and into the housing end 142. The channel 144 includes an inner wall 146 that is proximal or nearest to the upstream housing axis B. An outer wall 148 is spaced apart from inner wall 146, radially outward in a direction away from the upstream housing axis B. A bottom surface 150 of the channel extends between the inner wall 146 and the outer wall 148, and forms the second support surface 112. In some embodiments, the inner wall 146 forms the third support surface 114.

The annular channel 144 can have a cross-sectional shape with each of the inner wall 146 and the outer wall 148 can define a respective plane. The plane of the outer wall 148 extends transverse to the plane of the inner wall 146. The cross-sectional shape of the channel 144 can define a cross-sectional width that tapers away from the valve support surface 104. The cross-sectional shape can be any regular or irregular shape, including, for example, a square, a trapezoid, and a circle. In some embodiments, the annular channel 144 can comprise a convex and/or concave surface.

The bottom surface 150 of the annular channel 144 defines a length L1 (FIG. 7) that extends between the between the inner wall 146 and the outer wall 148. The length L1 can be at least about 0.02 inch and/or less than or equal to about 0.5 inch. Further, the length L1 can also be between about 0.04 inch and about 0.1 inch. In some embodiments of the present disclosure, the length L1 is any length that is greater than a cross-sectional width of the isolating bridge 120.

A portion of the upstream housing end 142, radially inward of the annular channel 144 defines a support hub 152 that forms the first support surface 110. The support hub 152 provides a surface for the valve to engage against and prevent unintended opening of the valve 102. For example, when a downstream fluid moves toward the valve 102, e.g., a backflow, a portion of the valve can engage against support hub 152 to prevent the valve from opening.

The first support surface 110 defines a plane that is aligned with the outer surface of the upstream housing end 142. In some embodiments of the present disclosure, the first support surface 110 can be offset from the upstream housing end 142 along the upstream housing axis B. In some aspects of the present disclosure, any of the support hub 152 and the first support surface 110 can comprise a convex and/or concave surface.

The support hub 152 includes an outer side surface defined by the inner wall 146. The outer side surface of the support hub 152 can have a cross-sectional length L2 extending between opposing sides of the inner wall 146. The length L2 (FIG. 7) can be at least about 0.1 inch and/or less than or equal to about 1.0 inch. Further, the length L2 can also be between about 0.2 inch and about 0.4 inch.

The upstream portion 132 of the passageway extends through the upstream housing end 142 to permit a fluid to move toward or away from the valve support surface 104. The upstream portion 132 of the passageway includes passages 154 that extends through the support hub 152. The passages 154 are oriented to extend through the first support surface 110.

The passages 154 form a longitudinal axis that are aligned relative to each other and the upstream housing axis B. For example, the longitudinal axis of each passage 154 is aligned parallel with each other with the upstream housing axis B. In some embodiments, the passages 154 are spaced apart around the upstream housing axis B and extend through the support hub 152.

The passages 154 comprise an arcuate cross-sectional profile shape. However, in some embodiments, the passages 154 can comprise any cross-sectional profile shape, including a circle or square. In some aspects, the passages 154 extend through the upstream valve housing 140 with a longitudinal axis that is transverse relative to the axis B. In yet another embodiment, a passage 154 extends through another portion of the upstream valve housing 140. For example, a passage 154 can extend through any of the first support surface 110, the inner wall 146, the outer wall 148, and the third support surface 114.

A portion of the upstream housing end 142, radially outward of the annular channel 144 forms an annular first valve retention surface 158. The first valve retention surface 158 is configured to engage against a portion of the valve 102 to resist movement of the portion of the valve relative to the upstream valve housing 140.

The first valve retention surface 158 can be shaped as a flat surface defining a plane. The plane of the first valve retention surface 158 is coincident with a plane defined by the upstream housing end 142. In some embodiments, the plane of the first valve retention surface 158 can be parallel or transverse to the upstream housing end 142. In some aspects of the present disclosure, first valve retention surface 158 can comprise a convex and/or concave surface.

When a valve 102 is coupled with the housing 106, the mounting rim 122 of the valve is engaged against the first valve retention surface 158. The mounting rim 122 is axially compressed between the first valve retention surface 158 and another portion of the housing 106, for example, a valve retention surface of the downstream valve housing 170.

Optionally, the housing 106 can include an annular valve retention wall 160. The valve retention wall 160 is configured to engage against a portion of the mounting rim 122 to restrict movement of the mounting rim 122 relative to the housing 106.

The valve retention wall 160 is positioned radially outward, relative to the first valve retention surface 110 and the second support surface 112. The valve retention wall 160 can extend way from the first valve retention surface 158. The valve retention wall 160 can have an inner surface 162 that faces toward the upstream housing axis B. The inner surface 162 of the valve retention wall 160 comprises a cross-sectional length that is less than a cross-sectional length defined by the outer surface of the mounting rim 122.

When a valve 102 is coupled with the housing 106, the outer surface of the mounting rim 122 engages against the inner surface of the valve retention wall 160. Because the cross-sectional length of the inner surface 162 of the valve retention wall is less than a length defined by the outer surface of the mounting rim 122, the mounting rim 122 is compressed radially inward.

In some embodiments, the valve retention wall 160 can extend from any of the upstream and the downstream valve housing 170. In yet another embodiment, any of the annular valve retention surface 158 and valve retention wall 160 can be formed by a channel or groove of the housing 106. In yet another embodiment, the valve retention wall 160 can be any of a series continuous or discontinuous protrusions and/or dimples.

In some embodiments, the valve support surface 104 is coupled to any of the upstream valve housing 140 and the downstream valve housing 170. In some aspects of the present disclosure, any of the upstream valve housing 140 and the downstream valve housing 170 comprise the valve support surface 104. For example, a check valve 100 can have an upstream valve support surface to resist movement of the valve toward the upstream housing 140, and a downstream valve support surface to resist movement of the valve toward the downstream housing 170.

Figure 4:
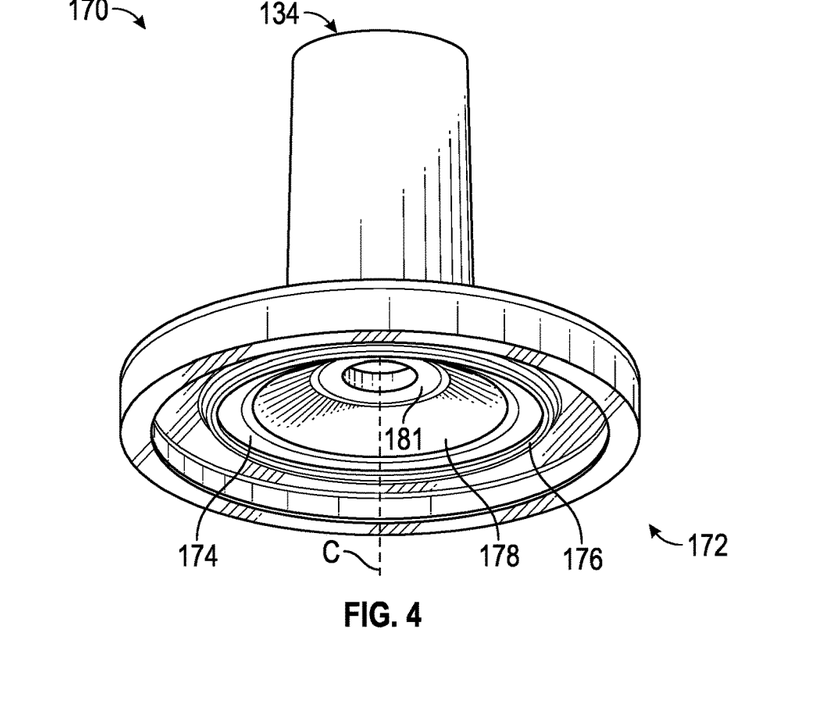
FIG. 4 is a perspective view of another housing of a diaphragm check valve, according to some embodiments.

The downstream valve housing 170 is shaped as a body having an end portion 172 and a fluid passage 130. The fluid passage can comprise the downstream portion 134 of the passageway. The downstream portion 134 of the passageway extends through the end portion 172, defining an upstream housing axis C. A fluid moving through the downstream portion 134 of the passageway is directed toward or away from the downstream housing end 172.

Referring to FIGS. 2 and 4, the end portion 172 forms a second annular valve retention surface 174 configured to engage a portion of the valve 102. The downstream portion 134 of the passageway extends through the end portion 172, defining a downstream housing axis C.

The downstream portion 134 of the passageway includes a passage 178 that extends through the end portion 172. The passage 178 is oriented to extend through the second annular valve retention surface 174. In some embodiments, the downstream portion 134 of the passageway forms a plurality of passages that extend through the end portion 172. The passage 178 comprises a length that extends from the end portion 172 into the downstream valve housing 170. A cross-sectional width of the passage 178 tapers away from the second annular valve retention surface 174.

In some embodiments, a portion of the passage 178, distal to the second annular valve retention surface 174, comprises an annular ridge 181 that extends into the downstream portion 134 of the passageway. The annular ridge 181 includes an inner surface defining a passage having a cross-sectional length or diameter. The annular ridge 181 can be configured to be engaged by a tube inserted into the downstream portion 134 of the passageway. Accordingly, a cross-sectional length of the passage through the annular ridge 181 is less than a cross-sectional length of a tube configured to be inserted into the check valve 100. In some embodiments, the diameter of the passage through the annular ridge 181 is configured to resist or restrict a rate of fluid flow through the downstream housing 170.

The second annular valve retention surface 174 includes a compression ridge 176 that is configured to direct a force toward the mounting rim 122 of the valve. The compression ridge 176 extends from the second annular valve retention surface 174 to engage against a portion of the mounting rim 122 to restrict movement of the mounting rim 122 relative to the housing 106.

The compression ridge 176 is shaped as a ridge that extends around the downstream housing axis C, and protrudes away from the second annular valve retention surface 174. The compression ridge 176 is positioned so that when the downstream valve housing 170 is coupled with the upstream valve housing 140, the compression ridge 176 extends from the second annular valve retention surface 174 toward the annular first valve retention surface 158.

The compression ridge 176 includes an outer surface that faces away the downstream housing axis C. The outer surface of the compression ridge 176 defines a cross-sectional length that is less than the cross-sectional length of the inner surface 162 of the valve retention wall. As a result, the compression ridge 176 is positioned radially inward from the valve retention wall 160 when the upstream valve housing 140 is coupled with the downstream housing 170.

In some embodiments of the present disclosure, the compression ridge 176 can be a protrusion or series of protrusions that extend from the second annular valve retention surface 174. In some embodiments, the compression ridge 176 can be any of a convex and concave portion of the second annular valve retention surface 174 and/or valve support surface 104.

The housing 106, or any portion thereof, can comprise a material that is configured to resist deformation during intended use of the check valve 100. For example, any of the upstream housing 140 and the downstream housing 170 may be rigid relative to the valve 102. The housing 106 can be more rigid than the valve 102, such that the housing 106 resists changing shape or size when the valve 102 is urged against the housing 106. In some embodiments, the material of the valve support surface 104 is configured to resist deformation during intended use of the check valve 100. For example, the material of the valve support surface 104 can be rigid relative to the valve 102.

The material of the housing 106 and/or the valve support surface 104 can be any of a plastic, a metal, a glass, a rubber, a composite, and any combination thereof. In some embodiments, the material can comprises any of a polycarbonate, a polyoxymethylene, an acrylonitrile butadiene styrene, an acrylic, and a copolyester.

Figure 5A:
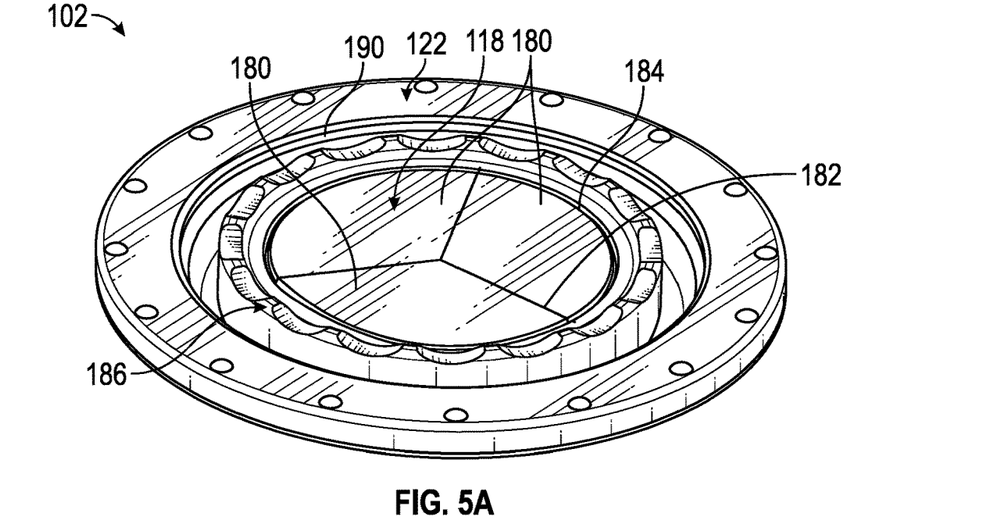
FIG. 5A is a top perspective view of a valve of a diaphragm check valve, according to some embodiments.
Figure 5B:
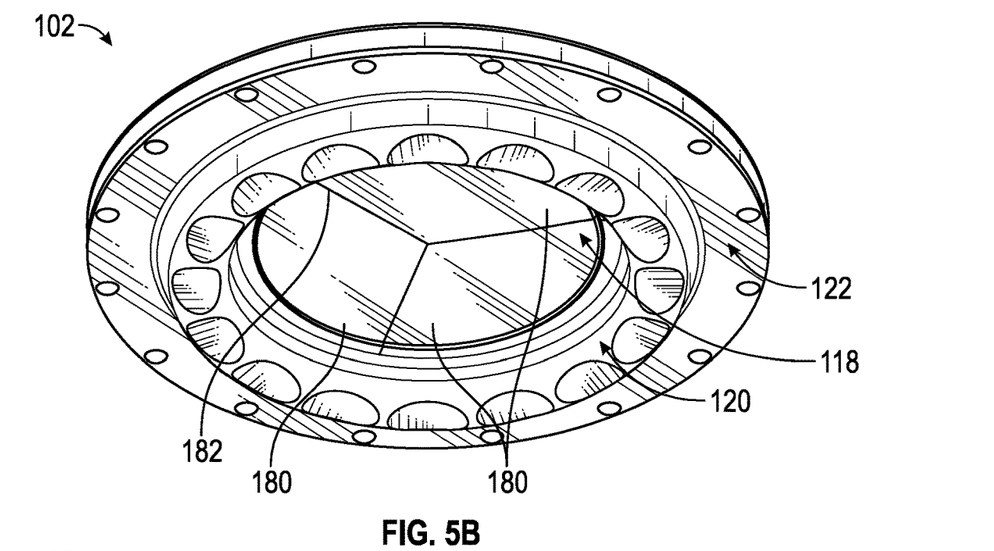
FIG. 5B is a bottom perspective view of a valve of a diaphragm check valve, according to some embodiments.
Figure 5C:
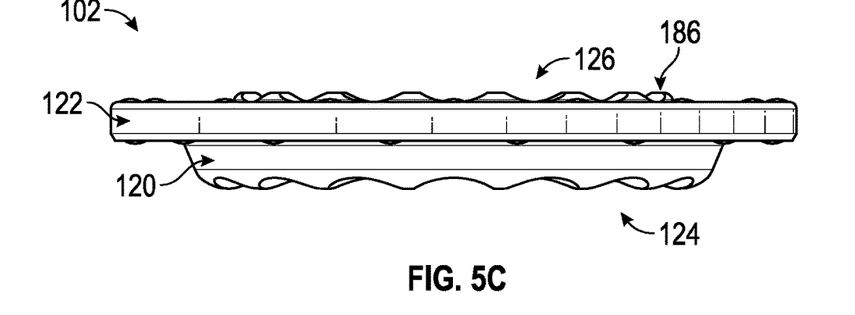
FIG. 5C is a side elevation view of a valve of a diaphragm check valve, according to some embodiments.
Figure 6:
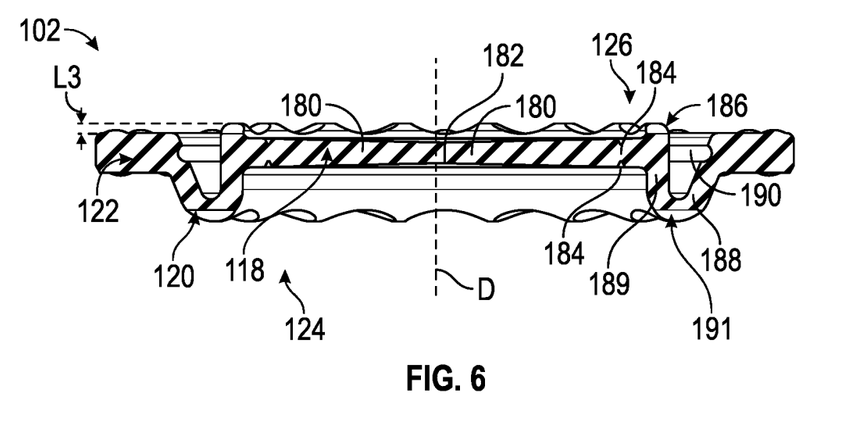
FIG. 6 is a cross-sectional side view of the valve of FIG. 5C.

Referring to FIGS. 5A-6, a valve 102 of the check valve is illustrated. The valve 102 is configured to form a diaphragm between portions of the fluid passageway 130. Further, the valve 102 can resist a movement of a fluid through the check valve 102, and can move to permit movement of a fluid through the check valve 102.

The valve 102 can have a first end portion 124 and a second end portion 126. The valve 102 includes a valve diaphragm 118, a mounting rim 122, and an isolating bridge 120. Although the valve 102 is illustrated as having a circular shape, the valve 102, and/or a portion thereof, can be any regular or irregular shape, including any of a circle, square, rectangle, and oval.

The valve diaphragm 118 is configured to permit or restrict fluid flow through the valve 102. The valve diaphragm 118 includes a valve segment 180 that can resist a fluid flow through the valve 102, and can permit a fluid flow through the valve 102. The valve segment 180 can be configured to move to resist a fluid flow through the valve 102, e.g., a normally open valve, or can move to permit a fluid flow through the valve 102, e.g., a normally closed valve.

The valve segment 180 is formed by a slit 182 that extends through the valve diaphragm 118. The slit 182 separates the valve diaphragm 118 into one or more valve segment 180. Each valve segment can extend from an outer portion of the valve diaphragm 118 toward an inner portion of the valve diaphragm 118, relative to a central valve axis D of the valve 102.

The valve segment 180 can have a cross-sectional height that is transverse to a length of the valve between the inner portion and the outer portion of the valve diaphragm 118. The cross-sectional height of the valve segment 180 tapers toward the valve axis D. In some embodiments, the cross-sectional height of the valve segment 180 is consistent along a length of the valve segment 180. In some embodiments, the cross-sectional height of the valve segment 180 tapers away from the valve axis D.

The slit 182 extends through the valve diaphragm 118, between outer side surfaces of the valve diaphragm 118. For example, the slit 182 can extend through the valve diaphragm 118, between the first end portion 124 and the second end portion 126 of the valve 102, and from the outer portion of the valve diaphragm 118 toward the inner portion of the valve diaphragm 118.

The valve diaphragm 118 can include more than one slit. For example, two slits 182 can intersect, forming more than one valve segment 180. In some embodiments, three slits extend radially outward, relative to a valve axis D. The slits 182 can be spaced apart forming valve segments 180 having an approximately equal length and width.

The slit 182 extends through the valve 102, relative to the valve axis D of the valve 102. More than one slit 182 can intersect at a point coincident with a valve axis D. However, it should be understood that a slit 182 can intersect at a point radially offset from a valve axis D.

The slit 182 can form a straight line, defining a plane that extends through the valve diaphragm 118. However, in some embodiments, any portion of a slit 182 can form any of a straight line, a curved line, and a line having alternating directions.

In some embodiments, the valve 102 includes two or more radial slits that form two or more petal-shaped valve segments that can open and close together. As maximum deflection of the valve segments 180 can occur at the center of the valve, e.g., the valve axis D, cumulative opening from the sum of the valve segments 180 can permit most particulates or debris to move through the valve 102 without becoming stuck or lodged in the valve 102.

In some aspects of the present disclosure, the valve 102 can comprise any type of valve segment to permit or resist fluid flow through the valve 102. For example, the valve 102 can include a hinged panel or plurality of layers configured to move to resist or permit a fluid flow. In another embodiment, the valve can be configured to be move when engaged by a fluid flow, wherein the movement of the valve open and/or closes a fluid passageway. In yet another embodiment, the valve can move to trigger another portion of the check valve to open or close a fluid passageway.

In some embodiments, the valve 102 includes a groove 184 that extends along a surface of the valve diaphragm 118 to increase the flexibility and range of movement of a valve segment 180. In some embodiments, the groove 184 can reduce or increase the cracking pressure of the valve 102, relative to a valve without grooves.

In some instances, the groove 184 extends along the outer portion of the valve diaphragm 118. The groove can extend into any of the first end portion 124 and the second end portion 126 of the valve 102. In some embodiments, the groove 184 can be shaped as any of a concave portion of the valve diaphragm 118 and a passage that extends through the diaphragm 118. In some embodiments, the valve diaphragm 118 comprises a protrusion that extend from any of the first end portion 124 and the second end portion 126 of the valve 102 to decrease the flexibility or range of movement of a valve segment 180.

The outer portion of the valve diaphragm 118 can include a protrusion configured to limit movement of the valve 102 relative to an adjacent structure such as the housing 106. The protrusion extends from the second end portion 126 of the valve 102, away from the valve diaphragm 118. The protrusion is shaped as an annular ridge 186 that extends along the outer portion of the valve diaphragm 118 and around the valve axis D.

The annular ridge 186 extends from the valve diaphragm 118 by a length L3. The length L3 can be at least about 0.001 inch and/or less than or equal to about 0.1 inch. Further, the length L3 can also be between about 0.004 inch and about 0.04 inch.

The annular ridge 186 can include a cutout that extend from an outer surface, into the annular ridge 186. The cutout is a scallop cutout that extends from a distalmost outer surface of the annular ridge 186 toward the valve diaphragm 118. However, the cutout can be any of a notch, passage, and channel that extend into the annular ridge 186.

In some embodiments, the annular ridge 186 can define discontinuous protrusions can extend away from the valve diaphragm 118. In some aspects, the valve 102 can comprise concentric protrusions or annular ridges. In yet another embodiment, the check valve 100 can comprise a protrusion that extends from the housing toward the valve 102 to resist movement of the valve 102. In some embodiments, the annular ridge 186 extends from any of the inner portion and the outer portion of the valve diaphragm 118.

In operation, the annular ridge 186 engages against the downstream housing 170 to resist movement of the valve 102. For example, when the valve is in an open position, pressure against the upstream or first end portion 124 of the valve causes the valve diaphragm 118 to move toward the downstream housing 170. To prevent unintended contact of the valve diaphragm 118 or a valve segment 180 against the downstream housing 170, the ridge 186 is configured to contact the downstream housing 170 before a portion of the valve diaphragm 118.

Further, limiting movement of the valve 102 can limit the distance to which the valve segments 180 can open. In some instances, the movement of the valve 102 is limited to resist opening the valve 102 more than necessary to achieve the minimum desire flow rate, the ridge 186. As a result, extraneous wear of the check valve 100 can be avoided.

The isolating bridge 120 of the valve is configured to resist the transfer forces radially inward relative to the isolating bridge 120. For example, radially and/or axial forces can be directed from the mounting rim 122 toward the valve diaphragm 118 when the valve 102 is coupled with the housing 108. The isolating bridge 120 resists the transfer of radial and axial forces toward the valve diaphragm 118, thereby preventing the valve segments 180 from becoming urged against each other and deformed or tenting, which can form gaps or passages through the valve diaphragm 118.

The isolating bridge 120 is annularly shaped and extends between the mounting rim 122 and the valve diaphragm 118. The isolating bridge 120 can be toroid shape having an arcuate cross-sectional profile shape.

The isolating bridge 120 includes a first bridge wall 188 that extends from the valve diaphragm 118 in a first direction, and a second bridge wall 189 that extends from the first bridge wall 188 in a second direction that is transverse to the first direction. The second bridge wall 189 extends from the first bridge wall 188 to the mounting rim 122. The intersection of the first and the second bridge wall can form an apex 191 of the isolating bridge. In some embodiments, the isolating bridge 120 wall extends in a direction that is radially and axially outward from the valve diaphragm 118.

The cross-sectional profile shape of the isolating bridge 120 defines a width. The width of the isolating bridge 120 is configured to prevent unintended contact between the isolating bridge and the support hub 152, which may otherwise cause the valve segments 180 to move apart and permit flow through the valve 102.

To prevent contact between the isolating bridge 120 and the support hub 152, the width of the isolating bridge 120 is less than a cross-sectional profile of the annular channel 144. For example, the width of the isolating bridge 120 is less than the length L1 of the bottom surface 150 of the annular channel 144 to prevent radially inward forces from causing engagement of the isolating bridge 120 to engage against the support hub 152, at least when the valve 102 is in a neutral or closed position.

The isolating bridge 120 can optionally include a cutout that extend from an outer surface into a bridge wall. The cutout of the isolating bridge 120 can contribute to the reduction of transfer of radial and axial forces toward the valve diaphragm 118. Further, the cutout can reduce the rigidity of the isolating bridge 120 relative to other portions of the valve 102.

The cutout is a scallop cutout that extends from outer surface at the apex 191 toward the valve diaphragm 118. However, the cutout can be any of a notch, passage, and channel that extend into the isolating bridge 120. Because the cutout forms an outer surface of the isolating bridge 120 having discontinuities, less surface are of the isolating bridge 120 engages against the second support surface 114.

In some embodiments, discontinuous protrusions can extend away from the isolating bridge 120. In some aspects, the check valve 100 can comprise a protrusion that extends from the housing or second support surface 114 toward the isolating bridge 120. In some embodiments, a cutout extends in a direction from any of the first end portion 124 and the second end portion 126 of the valve into the isolating bridge 120.

The mounting rim 122 is configured to engage against the housing or other retention feature to position the valve 102 in the check valve 100. Further, the mounting rim 122 is coupled to the housing so that a force is directed to the mounting rim 122 and moves toward the valve diaphragm 118 to maintain the valve segments 180 in a closed position. Accordingly, the mounting rim 122 can be compressed between surfaces of the housing 106, resulting in any of a radial and axial compression force directed to the mounting rim 122.

The mounting rim 122 is annularly shaped and extends radially outward from the isolating bridge 120. The mounting rim 122 can be toroid shape having a cross-sectional profile shape. The cross-sectional profile shape can be any regular or irregular shape, including any of a circle, square, rectangle, and oval.

The cross-sectional profile shape also defines an radial inner surface and an radial outer surface of the mounting rim 122. The inner surface faces radially inward toward the valve diaphragm 118.

In some embodiments, the inner surface includes a circumferential groove 190. The circumferential groove 190 extends along the circumference of the inner surface of the mounting rim 122. The circumferential groove 190 can contribute to the reduction of transfer of radial and axial forces toward the valve diaphragm 118. In some aspects, the circumferential groove 190 can increase ease of manufacturing and manufacturing efficiency by providing a location for the valve 102 to engage against and remain affixed to a mold that forms the valve 102.

In some embodiments, a protrusion extends from an outer surface of the mounting rim 122. The protrusion can extend radially outward from the outer surface of the mounting rim 122. A plurality of discontinuous radially extending protrusions can limit the transfer of radial compression to the valve 102 over periodic segments. In some embodiments, the protrusions can be formed by scallop cutouts that extend into the mounting rim 122. In some aspects, the scallop cutouts can extends in a direction from the first end portion 124 and/or the second end portion 126 of the valve into a the mounting rim 122.

The mounting rim 122 can optionally include a protrusion that extends in a direction away from the first end portion 124 and/or the second end portion 126 of the valve. For example, the protrusion can extend toward any of the annular first valve retention surface 158 and the second annular valve retention surface 174 when the valve 102 is coupled with a housing 106.

The valve 102 can comprise any flexible or resilient material, and can include any of a plastic, a rubber, a composite, and any combination thereof. A material of the valve 102 can include any of a thermoset material, such as polyisoprene, and a thermoplastic material. In some embodiments of the present disclosure, the valve comprises a material having a Shore hardness rating of at least about 20 and/or less than or equal to about 80.

In some embodiments, one or more portion of the valve 102 can comprise a different material or material characteristic than another portion. For example, the valve diaphragm 118, or any portion thereof, can comprise a material that is configured to resiliently deform during intended use of the check valve 100. In some aspects, the valve diaphragm 118 can be more flexible, relative to the isolating bridge 120 and the mounting rim 122, so that the valve diaphragm 118 is resiliently moved before another portion of the valve 102.

Figure 7:
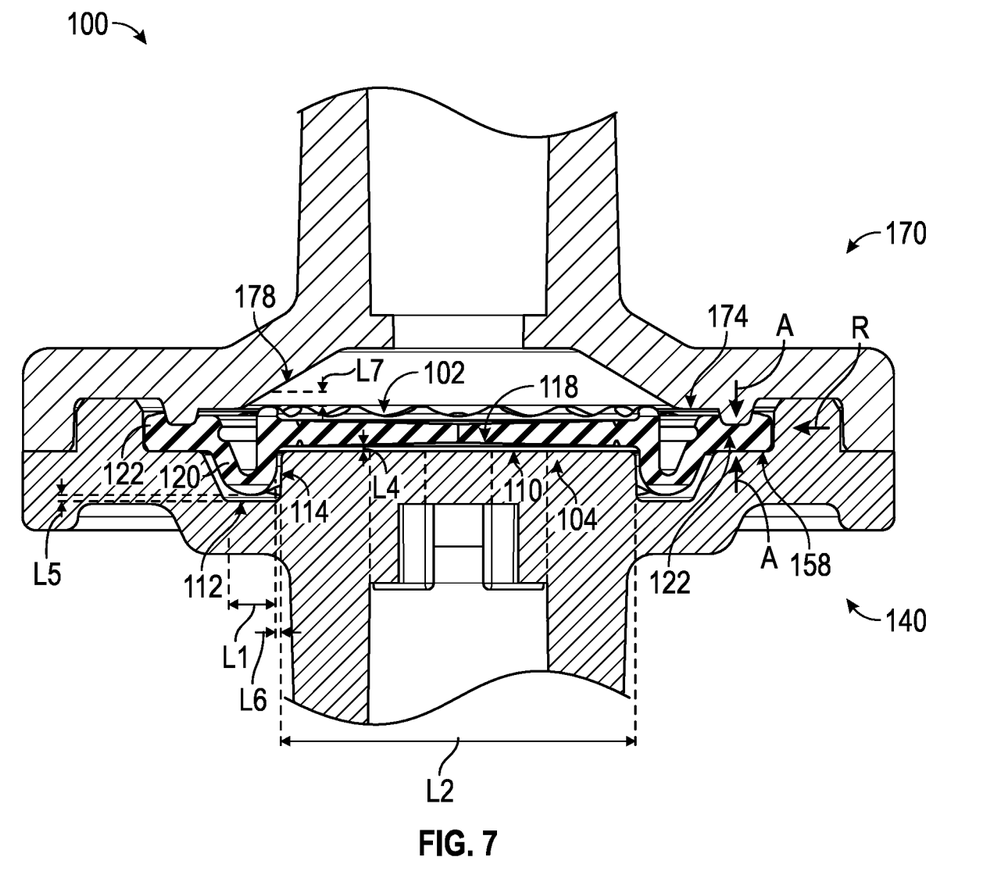
FIG. 7 is a cross-sectional detail view of the diaphragm check valve of FIG. 1.

FIG. 7 illustrates the valve 102 in a closed or neutral position. The valve 102 is positioned adjacent to the valve support surface 104 with the first end portion 124 of the valve facing the valve support surface 104. The valve 102 is positioned with the valve diaphragm 118 adjacent to the first support surface 110, and the isolating bridge 120 adjacent to the second support surface 112.

The mounting rim 122 is positioned between the annular first valve retention surface 158 and the second annular valve retention surface 174, and radially inward relative to the valve retention wall 160. The first valve retention surface 158 and the second valve retention surface 174 direct an axial compression force (A arrows) toward the mounting rim 122. The valve retention wall 160 directs a radial compression force (R arrow) toward the mounting rim 122.

The isolating bridge 120 reduces the axial and/or radial compression force transferred from the mounting rim 122 inward toward the valve diaphragm 118. For example, if the mounting rim 122 is compressed radially inward by about 0.004 inch, the isolating bridge 120 can cause the valve diaphragm 118 or other portion of the valve 102 to be compressed radially inward by about 0.00005 inch. The reduction of radial compression directed toward the valve diaphragm 118 permits the valve segments 180 to engage each other to seal or close the fluid passageway through the valve 102, yet prevents the valve segments 180 from buckling or tenting and thereby forming a gap between the valve segments 180.

The valve 102 and the valve support surface 104 are configured with a portion of the valve 102 spaced apart from a portion of the valve support surface 104. Spacing between portions of the valve 102 and the valve support surface 104 ensure that the check valve operates as intended.

The first support surface 110 is spaced apart from the nearest surface of the valve diaphragm 118 by a distance L4, and the second support surface 112 is spaced apart from the nearest surface of the annular isolating bridge 120 by a distance L5. To prevent the valve diaphragm 118 from engaging the first support surface 110, the distance L4 is greater than the distance L5. The distance L5 can be at least about 0.001 inches and/or less than or equal to about 0.1 inch. Further, the distance L5 can also be between about 0.002 inch and about 0.04 inch. In some embodiments of the present disclosure, the distance L5 is zero inches.

In operation, when the valve 102 moves toward the valve support surface 104, the isolating bridge 120 engages the second support surface 112 before the valve diaphragm 118 can engage the first support surface 110.

The third support surface 114 is spaced apart from the nearest surface of the isolating bridge 120 by a distance L6. The distance L6 can be at least about 0.001 inches and/or less than or equal to about 0.1 inch. Further, the distance L6 can also be between about 0.002 inch and about 0.02 inch.

The space between the third support surface 114 and the isolating bridge 120 can permit the valve 102 to receive any of a radial and an axial force, yet resist engagement of the isolating bridge 120 against the third support surface 114.

The annular ridge 186 is spaced apart from the nearest surface of the downstream housing 170 by a distance L7. The distance L7 can be at least about 0.001 inches and/or less than or equal to about 0.1 inch. Further, the distance L7 can also be between about 0.004 inch and about 0.04 inch.

In operation, when the valve 102 moves away from the valve support surface 104, the distance L7 can permit the valve diaphragm 118 to move toward the downstream housing 170 and the valve to open, yet the annular ridge 186 can engage against the downstream housing 170 to resist further movement of the valve 102.

Figure 8A:
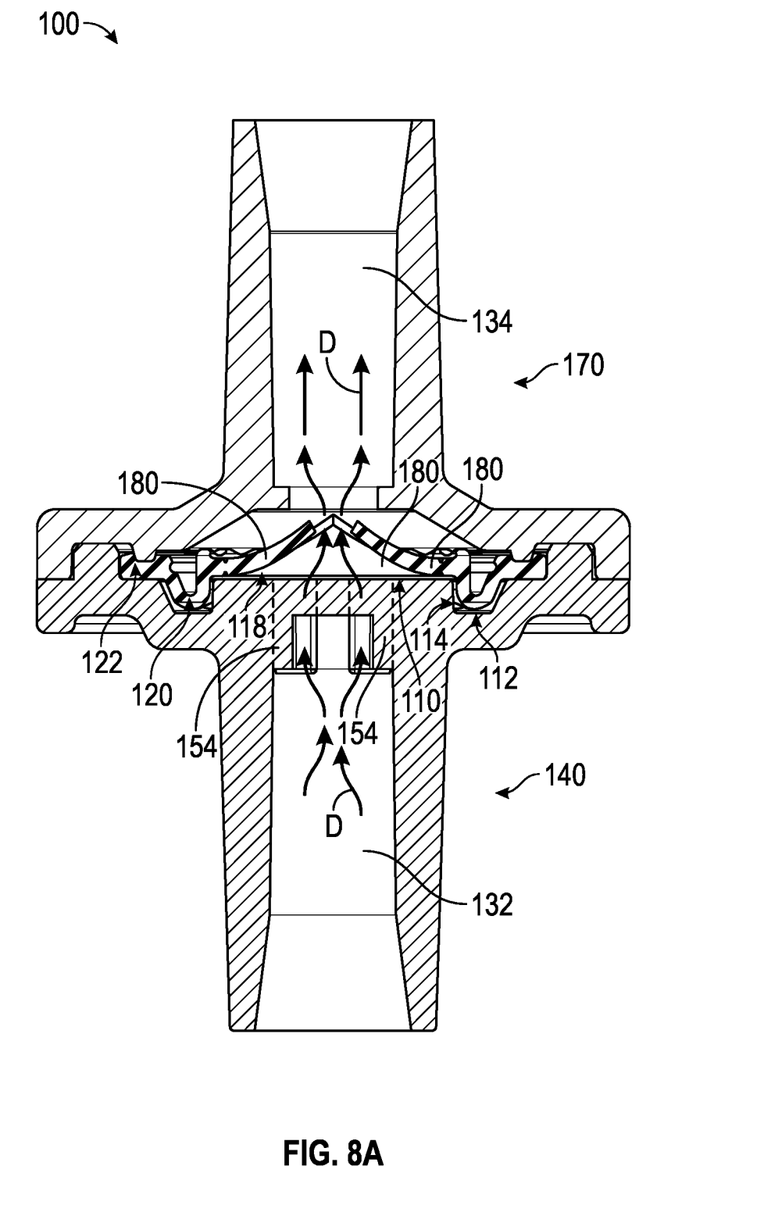
FIG. 8A is a cross-sectional view of a diaphragm check valve in an open position, according to some embodiments.

Referring to FIG. 8A, the check valve 100 is illustrated in an open position with a downstream fluid flow (D arrows) moving through the valve 102. In the open position, a downstream fluid flow D can move from the upstream portion 132 of the passageway, through the passages 154 and valve 102, toward the downstream portion 134 of the passageway.

In the open position, a pressure from the fluid has engaged against the first end portion 124 of the valve 102, and caused at least a portion of the valve 102 to move away from the valve support surface 104 toward the downstream housing 170. More specifically, the valve segments 180 have been urged toward the downstream housing 170. A portion of the valve segments 180 have moved, relative to each other, to form a fluid passageway through the valve 102.

The pressure engaged against the first end portion 124 of the valve 102 can cause the valve diaphragm 118 to move toward the downstream housing 170. As the valve diaphragm 118 moves toward the downstream housing 170, the distance L7, between the annular ridge 186 and the downstream housing 170 decreases. Optionally, the distance L7 can be configured so that the annular ridge 186 engages against the passage 178 when a pressure against the first end portion 124 of the valve exceeds the desired pressure or flow through the valve 102. In some embodiments, when the annular ridge 186 engages against the downstream housing 170, further opening or movement of the valve segments 180 toward the downstream housing 170 is resisted. Optionally, engagement of the isolating bridge 120 against a support surface, for example, the third support surface 114, can limit movement of the valve 102 relative to the valve support surface 104.

By limiting movement of the valve 102 in the open position, damage to the valve can be prevented. For example, fluid flow or pressure can cause the valve 102, or the valve diaphragm 118, to become stretched or deformed. Further, contact of the valve diaphragm 118 against another portion of the check valve 100, or other structure, can cause damage or changes in operational characteristics. Limiting movement of the valve 102 in the open position can resist damage or unintended changes in operation of the valve 102. In the open position, the valve diaphragm 118 permits a fluid to move through the valve 102, from the upstream portion 132 of the passageway toward the downstream portion 134 of the passageway.

Figure 8B:
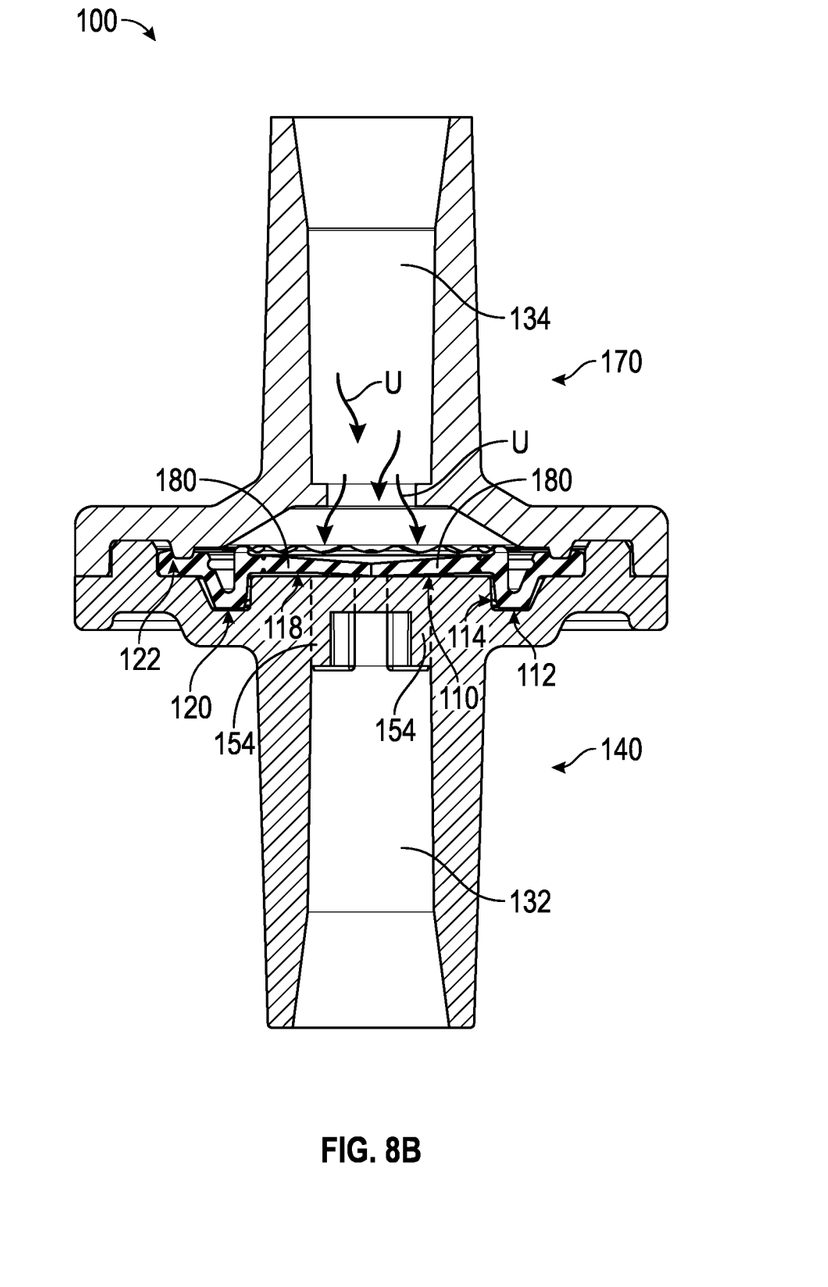
FIG. 8B is a cross-sectional view of a diaphragm check valve in a closed position, according to some embodiments.

Referring to FIG. 8B, the check valve 100 is illustrated in a closed position with a downstream fluid flow (U arrows). The downstream fluid flow U can be cause by a backflow of fluid from the downstream portion 134 of the passageway toward the valve 102. The downstream fluid flow U can direct a pressure against the valve 102, causing any of the valve segments 180, the valve diaphragm 118, and the isolating bridge 120 to move toward the first support surface 104.

When the valve segments 180 move toward the first support surface 104, the valve segments 180 engage each other to close the fluid passage through the valve 102. Further movement of the valve diaphragm 118 toward the first support surface 104 can cause the valve diaphragm 118 and/or the valve segments 180 to engage against the first support surface 110. Engagement of the valve diaphragm 118 against the first support surface 110 can assist with maintaining the valve diaphragm in the closed position. However, engagement of the valve diaphragm 118 against the first support surface 110 can also cause the valve to stretch and a passage through the valve diaphragm 118 to open, thereby permitting fluid flow through the valve 102.

To resist opening of the valve 102 or stretching of the valve diaphragm 118 in the closed position, a portion of the valve 102 engages the valve support surface 104 to resist movement of the valve 102 and prevent damage to the valve 102. More specifically, the isolating bridge 120 engages against the second support surface 112 before the valve diaphragm 118 engages against the first support surface 110. In some embodiments, engagement of the isolating bridge 120 against the second support surface 112 prevents the outer portion of the valve diaphragm 118 from engaging against the first support surface 110.

Engagement of the isolating bridge 120 against the second support surface 112 can prevent pressure engaged against valve from causing damage or a change in operation to the valve diaphragm 118. Damage or a change in operation to the valve diaphragm 118 can occur when engagement of the valve diaphragm 118 against the second support surface 110 causes the valve diaphragm 118 to stretch or deform, thereby creating a fluid passage between the valve segments 180, and permitting a fluid flow (e.g., backflow) to move through the valve 102.

Illustration of Subject Technology as Clauses

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. A check valve assembly comprising: a valve support surface having a first support surface and a second support surface, the second support surface positioned radially outward, relative to the first support surface; and a valve having: a mounting rim; a valve diaphragm extending radially inward from the mounting rim, and having a valve segment defined by a slit; and an annular isolating bridge extending between the mounting rim and the valve diaphragm; wherein a distance from the first support surface to the nearest surface of the valve diaphragm is greater than a distance from the second support surface to the nearest surface of the annular isolating bridge.

Clause 2. The check valve assembly of Clause 1, comprising an annular first valve retention surface and a second annular valve retention surface, the first and second valve retention surface positioned radially outward, relative to the second support surface.

Clause 3. The check valve assembly of Clause 2, wherein the mounting ring comprises a first end surface and a second end surface, opposite the first end surface, and wherein the first valve retention surface engages against the first end surface, and the second valve retention surface engages against the second end surface, to axially compress the mounting rim therebetween.

Clause 4. The check valve assembly of Clause 2, wherein any of the first and second valve retention surface comprises a compression ridge that extends toward the other of the first and second valve retention surface.

Clause 5. The check valve assembly of Clause 1, comprising an annular valve retention wall that is positioned radially outward, relative to the second support surface, wherein the annular valve retention wall engages against an outer surface of the mounting rim to direct the mounting rim radially inward.

Clause 6. The check valve assembly of Clause 5, wherein an inner surface of the annular valve retention wall comprises a cross-sectional length that is less than a cross-sectional length defined by the outer surface of the mounting rim.

Clause 7. The check valve assembly of Clause 1, comprising a fluid passageway that extends through the first support surface.

Clause 8. The check valve assembly of Clause 1, wherein the valve diaphragm comprises an outer portion and an inner portion, and the valve segment extends from the outer portion toward the inner portion.

Clause 9. The check valve assembly of Clause 8, wherein the valve diaphragm comprises an annular groove extending between the outer and inner portion.

Clause 10. The check valve assembly of Clause 1, wherein the valve diaphragm comprises a first end portion and a second end portion, and a protrusion that extends away from the second end portion.

Clause 11. The check valve assembly of Clause 10, wherein the protrusion is an annular ridge that extends along an outer portion of the valve diaphragm.

Clause 12. The check valve assembly of Clause 1, wherein the annular isolating bridge comprises an arcuate cross-sectional profile.

Clause 13. The check valve assembly of Clause 1, wherein the annular isolating bridge comprises a first bridge wall extending from the mounting rim in a first direction, and a second bridge wall extending from the first bridge wall in a second direction transverse to the first direction.

Clause 14. The check valve assembly of Clause 13, wherein the second bridge wall extends from the first bridge wall to the valve diaphragm.

Clause 15. The check valve assembly of Clause 13, wherein an apex of the annular isolating bridge is formed by an intersection of the first bridge wall and the second bridge wall.

Clause 16. The check valve assembly of Clause 1, wherein the annular isolating bridge comprises an outer surface having a scallop cutout.

Clause 17. The check valve assembly of Clause 1, wherein the annular isolating bridge comprises an outer surface having a protrusion.

Clause 18. The check valve assembly of Clause 1, wherein the valve support surface comprises an annular channel having a channel wall extending between the first support surface and a bottom surface.

Clause 19. The check valve assembly of Clause 18, wherein the channel wall defines a third support surface, and the bottom surface defines the second support surface.

Clause 20. A method of controlling flow through a check valve assembly comprising: defining a fluid passageway having a valve support surface, wherein the valve support surface comprises a first support surface and a second support surface, the second support surface radially outward, relative to the first support surface; positioning a valve adjacent to the valve support surface, wherein the valve comprises a valve diaphragm configured to resist a fluid flow through the fluid passageway, the valve diaphragm having a valve segment defined by a slit, and an annular isolating bridge extending radially outward from the valve diaphragm; wherein, when the valve is moved toward the valve support surface, the isolating bridge engages the second support surface before the valve diaphragm engages the first support surface.

Further Considerations

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

In one or more aspects, the terms "about," "substantially," and "approximately" may provide an industry-accepted tolerance for their corresponding terms and/or relativity between items.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope of the present disclosure. Unless otherwise expressed, reference to an element in the singular is not intended to mean "one and only one" unless explicitly stated, but rather is meant to mean "one or more." In addition, it is not necessary for a device or method to address every problem that is solvable (or possess every advantage that is achievable) by different embodiments of the disclosure in order to be encompassed within the scope of the disclosure. The use herein of "can" and derivatives thereof shall be understood in the sense of "possibly" or "optionally" as opposed to an affirmative capability.

What is claimed is:

1. A check valve assembly comprising:
an upstream valve support surface comprising a first surface portion and a second surface portion, the first surface portion having a fluid passageway that extends therethrough, and the second surface portion positioned radially outward from the first surface portion and extending around a perimeter of the first surface portion, wherein the second surface portion is spaced apart from the first surface portion in an upstream direction; and
a valve comprising a mounting rim, a valve diaphragm, and an annular isolating bridge extending between the mounting rim and the valve diaphragm, the valve positioned with the annular isolating bridge longitudinally aligned with the second surface portion, and the valve diaphragm longitudinally aligned with the first surface portion, wherein an upstream facing surface of the annular isolating bridge is spaced apart from an upstream facing surface of the valve diaphragm in the upstream direction, and a distance between the first surface portion and the second surface portion is less than a distance between the upstream facing surfaces of the valve diaphragm and the annular isolating bridge.

2. The check valve assembly of claim 1, wherein the valve diaphragm extends radially inward from the mounting rim.

3. The check valve assembly of claim 1, wherein a downstream facing surface of the valve diaphragm comprises a protrusion that extends away from the upstream valve support surface.

4. The check valve assembly of claim 1, wherein an apex of the annular isolating bridge comprises an outer surface having a protrusion.

5. The check valve assembly of claim 1, wherein the upstream valve support surface comprises an inner wall that extends between the first and second surface portions and is configured to resist movement of the annular isolating bridge radially inward.

6. The check valve assembly of claim 1, wherein the upstream valve support surface comprises an outer wall that extends to the second surface portion and is configured to resist movement of the annular isolating bridge radially outward.

7. The check valve assembly of claim 1, wherein the fluid passageway is spaced apart from a central axis through the first surface portion.

8. The check valve assembly of claim 1, comprising an annular valve retention wall that is positioned radially outward, relative to the second surface portion, wherein the annular valve retention wall engages against an outer surface of the mounting rim to direct the mounting rim radially inward.

9. The check valve assembly of claim 8, wherein an inner surface of the annular valve retention wall defines a cross-sectional length that is less than a cross-sectional length defined by the outer surface of the mounting rim.

10. A check valve assembly comprising:
  an upstream valve support surface comprising a first surface portion and a second surface portion, the first surface portion having a fluid passageway that extends therethrough, and the second surface portion positioned radially outward from the first surface portion and extending around a perimeter of the first surface portion, wherein the second surface portion is spaced apart from the first surface portion in an upstream direction; and
  a valve comprising a mounting rim, a valve diaphragm, and an annular isolating bridge extending between the mounting rim and the valve diaphragm, the valve positioned with the annular isolating bridge longitudinally aligned with and extending toward the second surface portion, and the valve diaphragm longitudinally aligned with the first surface portion, wherein, when the valve moves toward the upstream valve support surface, the annular isolating bridge engages against the second surface portion before the valve diaphragm engages against the first surface portion.

11. The check valve assembly of claim 10, wherein the valve diaphragm extends radially inward from the mounting rim.

12. The check valve assembly of claim 10, comprising an annular valve retention wall that is positioned radially outward, relative to the second surface portion, wherein the annular valve retention wall engages against an outer surface of the mounting rim to direct the mounting rim radially inward.

13. The check valve assembly of claim 10, wherein a downstream facing surface of the valve diaphragm comprises a protrusion that extends away from the upstream valve support surface.

14. The check valve assembly of claim 10, wherein an apex of the annular isolating bridge comprises an outer surface having a protrusion.

15. The check valve assembly of claim 10, wherein the upstream valve support surface comprises an inner wall that extends between the first and second surface portions and is configured to resist movement of the annular isolating bridge radially inward.

16. The check valve assembly of claim 10, wherein the upstream valve support surface comprises an outer wall that extends to the second surface portion and is configured to resist movement of the annular isolating bridge radially outward.

17. The check valve assembly of claim 10, wherein the fluid passageway is spaced apart from a central axis through the first surface portion.

18. A check valve assembly comprising:
  an upstream valve housing and a downstream valve housing, the upstream valve housing having an upstream valve support surface comprising a first surface portion and a second surface portion, the first surface portion having a fluid passageway that extends therethrough, and the second surface portion positioned radially outward from the first surface portion and extending around a perimeter of the first surface portion, wherein the second surface portion is spaced apart from the first surface portion in an upstream direction; and
  a valve comprising a mounting rim, a valve diaphragm, and an annular isolating bridge extending between the mounting rim and the valve diaphragm, the valve positioned between the upstream valve housing and the downstream valve housing with the annular isolating bridge longitudinally aligned with the second surface portion, and the valve diaphragm longitudinally aligned with the first surface portion, such that, the annular isolating bridge is configured to engage against the second surface portion when a fluid flow from the downstream valve housing engages against the valve diaphragm.

19. The check valve assembly of claim 18, wherein the upstream valve support surface comprises an inner wall that extends between the first and second surface portions and is configured to resist movement of the annular isolating bridge radially inward.

20. The check valve assembly of claim 18, wherein the upstream valve support surface comprises an outer wall that extends to the second surface portion and is configured to resist movement of the annular isolating bridge radially outward.

* * * * *